United States Patent [19]
Ericsson

[11] Patent Number: 4,764,373
[45] Date of Patent: Aug. 16, 1988

[54] METHOD OF INCREASING THE ECONOMIC VALUE OF BREEDING STOCK SEMEN

[75] Inventor: Ronald J. Ericsson, Ranch in Crook County, Wyo.

[73] Assignee: Gametrics Limited, Alzada, Mont.

[21] Appl. No.: 802,889

[22] Filed: Nov. 29, 1985

[51] Int. Cl.$^4$ .................. A61K 35/52; A01N 1/02
[52] U.S. Cl. ............................ 424/105; 435/2
[58] Field of Search ............................ 424/105; 435/2

[56] References Cited

U.S. PATENT DOCUMENTS

| | | | |
|---|---|---|---|
| 4,007,087 | 2/1977 | Ericsson | 195/1.8 |
| 4,009,260 | 2/1977 | Ericsson | 424/105 |
| 4,326,026 | 4/1982 | Sarkar | 424/105 |
| 4,339,434 | 7/1982 | Ericsson | 424/105 |

OTHER PUBLICATIONS

White, I. G., et al, "Reproduction in Sheep", Australian Academy of Science, (Dec. 1984), pp. 299, 300.

*Primary Examiner*—Sam Rosen
*Attorney, Agent, or Firm*—Millen & White

[57] ABSTRACT

Method of artificially inseminating a plurality of animals with aliquots of sperm obtained from a breeding stock individual of that species, obtained by fractionating the collected semen into first and second motile-sperm containing fractions, the first of which is free from immotile sperm and non-sperm components, both suspended in a liquid vehicle which is physiologically acceptable to the sperm and for artificial insemination; dividing the first and second fractions into a plurality of aliquots, each of which contain enough motile sperm to ensure a pregnancy when used for an artificial insemination; artificially inseminating a plurality of individuals of that species in which a predominance of male offspring is desired with the aliquots of the first fraction; and artificially inseminating a plurality of individuals of that species in which a predominance of male offspring is not a desired objective with the aliquots of the second fraction.

15 Claims, No Drawings

METHOD OF INCREASING THE ECONOMIC VALUE OF BREEDING STOCK SEMEN

BACKGROUND OF THE INVENTION

This invention relates to a method for increasing the economic value of breeding stock semen.

In mammals, the sex is determined by two different types of sperm, which have either an X-chromosome (X-sperm) or Y-chromosome (Y-sperm). The economic impact of sex preselection in livestock is well documented. See "Impacts of Applied Genetics, Micro-Organisms, Plants and Animals" Chapter 9, 1981, OTA Report. Lib. Congress Cat. Card No. 81-600046; R. J. Gerrits et al, "Economics of Improving Reproductive Efficiency in Farm Animals".

In U.S. Pat. No. 4,009,260, I claim methods for increasing the incidence of males in the offspring of mammals by artificially inseminating a fertile female with a Y-sperm enriched sperm fraction of that mammal obtained by maintaining at least the sperm portion of progressively motile sperm-containing semen, either as such or suspended in an aqueous suspending vehicle physiologically acceptable to the sperm, as an upper layer in vertical interfacial contact, at a temperature at which the motile sperm are motile, with a lower discrete layer of a first aqueous contacting medium physiologically acceptable to the sperm and in which the motile sperm migrate downwardly at a slower rate than the upper layer, until a portion only of the motile sperm of the semen has migrated downwardly into the contacting medium, thereby producing a contacting medium containing a higher proportion of Y to X sperm than in the starting sperm, and repeating the step at least once, employing in the upper layer the motile sperm which have migrated to the first aqueous contacting medium and as the lower layer of second aqueous contacting medium physiologically acceptable to the sperm and in which the motile sperm migrate downwardly at a slower rate than in the first contacting medium.

This method has gained acceptance in human clinics but its usage in animal husbandry has been limited by the fact that a significant proportion of the motile sperm of the fractionated semen is "wasted", i.e., that portion not in the Y-sperm enriched fraction or fractions. In other words, the economic gain achieved by producing a higher incidence of male offspring is partially offset by the inherently higher cost of Y-sperm enriched portion of the breeding stock sperm resulting from the "wasting" of a portion thereof in the patented process as well as the cost of fractionating the sperm to obtain an X-sperm enriched fraction.

Such a method would be economically more attractive for use with livestock herds if the number of inseminations achievable from an ejaculate were not substantially reduced by the patented fractionation process. However, the patented method is directed to maximizing the ratio of motile sperm to immotile sperm rather than maximizing the recovery of starting motile sperm since, in human beings at least, all other factors being equal the higher the ratio of motile sperm to immotile sperm in the seminating fluid, the greater the likelihood of a successful insemination therewith. In maximizing the ratio of motile to immotile sperm, a significant portion of the starting motile sperm is inherently lost.

In U.S. Pat. No. 4,339,434, I claim a method of increasing the likelihood of conceiving a female fetus by promoting ovulation in a fertile female mammal with an ovulation-inducing agent and then artificially inseminating the female mammal during the period of expected ovulation with a sperm fraction of enhanced sperm motility from which immotile sperm and non-sperm seminal components have been separated and which is suspended in serum albumin or like physiologically acceptable vehicle. This process also inherently "wastes" a portion of the starting motile sperm, since some of the motile sperm remains in the fraction containing the immotile sperm and non-sperm seminal components.

In U.S. Pat. No. 4,007,087, I claim a method for enhancing the survival rate of sperm subjected to frozen storage by subjecting sperm to the above-described fractionation methods prior to freezing. However, that invention makes no use of the motile sperm which is not present in the motile-sperm enriched fraction.

I have found that my above-described fractionation processes can be employed to enhance the total economic value of breeding stock semen, beyond that achievable when only the motile-sperm enriched the fraction thereof is employed.

The successful use of both the fraction of sperm enriched in motile sperm and the fraction of sperm separated from the motile enriched fraction, in accordance with the instant invention, to achieve a higher incidence of female offspring, respectively, in sheep has been reported by I. G. White, et al. in "Reproduction in Sheep", Lindsay, D. R. and Pearce, D. T., Supervising editors, Brinda Fulla Press and Pub. Pty. Ltd., Canberra ACT Australia, pp. 299–300 (Dec. 1984).

SUMMARY OF THE INVENTION

According to this invention, a plurality of animals are artificially inseminated with aliquots of sperm obtained from a breeding stock individual of that species, each of which contains a population of motile sperm large enough to ensure successful insemination therewith, which aliquots are obtained by the steps of (a) fractionating the collected semen into a first fraction from which the immotile sperm and non-sperm components have been separated and which contains from about 10% to about 80% of the motile sperm of the semen, suspended in a liquid vehicle which is physiologically acceptable to the sperm and for artificial insemination, and into a second fraction, containing the remainder of the motile sperm thereof, also suspended in a liquid vehicle which is physiologically acceptable to the sperm and for artificial insemination; (b) dividing the first fraction into a plurality of aliquots, each of which contain a population of motile sperm large enough to ensure a pregnancy when used for an artificial insemination; (c) dividing the second fraction into a plurality of aliquots, each of which contain a population of motile sperm large enough to ensure a pregnancy when used for an artificial insemination; (d) artificially inseminating a plurality of individuals of that species in which a predominance of male offspring is desired with the aliquots of the first fraction; and artificially inseminating a plurality of individuals of that species in which a predominance of male offspring is not a desired objective with the aliquots of the second fraction.

DETAILED DISCUSSION

The present invention is based on the discovery that, unlike the human species, with husbandry species of animals, e.g., bovine, ovine, and equine, both the fraction of sperm enriched in motile sperm and the fraction depleted in motile sperm obtained according to my patented fractionation process, can be used commercially for the successful artificial insemination of herds of animals of that species of animal, provided the aliquots thereof employed to inseminate contain a large enough population of motile sperm to ensure successful insemination. This is surprising because sperm with an abnormally low proportion of motile to immotile sperm is considered inferior at best commercially and an individual of that species with such defective sperm is not ordinarily used for breeding purposes, especially for herd upgrading. It is further surprising because a successful artificial insemination commercially of a herd of animals requires that 50% or more of the inseminated animals become pregnant. One would expect that a fraction of semen a majority of whose motile sperm has been separated therefrom would be at best only marginally fertile. Surprisingly, this is not the case, which means that the loss of sperm heretofore believed to be inherent in the practice of any patented fractionation processes is not obligatory, thereby making those processes economically significantly more attractive, especially when the semen is obtained from a breeding stock individual.

In a preferred embodiment, the sperm is fractionated according to the processes of U.S. Pat. Nos. 4,007,087 and 4,009,260, whose disclosures are incorporated herein by reference, viz., separating motile sperm from immotile sperm by maintaining at least the sperm portion of progressively motile sperm-containing semen, either as such or preferably as a suspension in an aqueous vehicle physiologically acceptable to the sperm as an upper layer in vertical interfacial contact with a discrete lower layer of an aqueous contacting medium physiologically acceptable to the sperm in which the motile sperm has a lower migration rate than in the upper layer, until motile sperm of the semen have migrated into the contacting medium, thereby producing a contacting medium containing a sperm fraction having a higher proportion of motile sperm with enhanced Y-sperm content.

In one embodiment of the aforesaid fractionation processes, the whole semen is employed as starting material for the aforesaid fraction process.

In another embodiment of the aforesaid sperm fractionation process, the fractionation is repeated with the thus-obtained lower, motile-sperm enriched fraction and a second contacting medium in which the motile sperm have a still lower migration rate than in the first contacting medium, produces a sperm fraction consisting predominantly of motile Y-sperm. In such a preferred embodiment, the upper motile-sperm depleted fraction from the second fractionation is combined with the upper motile-sperm depleted fraction from the first fractionation.

Motile sperm is separated from immotile sperm in the first fractionation, thereby providing a highly motile sperm fraction of enhanced content of motile Y-sperm and normal morphology, thereby greatly enhancing the quality of the sperm.

In U.S. Pat. No. 4,007,087, I note that conventionally in the artificial insemination of animals, e.g., mares and cows, diluted stored semen is introduced directly in the uterus and that although the incidence of unsuccessful inseminations is relatively low, a significant number of inseminations are unsuccessful and require repeat insemination, resulting in economic loss to the owner of the animal due to the delay in pregnancy and to the inseminator who must repeat the insemination. I express a belief that these unsuccessful inseminations are at least partially due to the introduction into the uterus of animals stored semen containing a high proportion of immotile, defective and dead sperm and their decomposition products.

It is surprising therefore, that the rate of successful impregnations with aliquots of the top, motile sperm depleted fraction of the starting semen is comparable to that achieved with aliquots of unfractionated whole semen obtained from the same source, stored in the same manner and containing the same population of motile-sperm per aliquot, even though the ratio of motile to immotile sperm in the fractionated top portion is significantly lower than that of the comparable stored whole semen.

The motile-sperm depleted fraction can be used for the insemination of breeds of the species of animal where a predominance of male offspring is not a desired objective or breeds of the species where a predominance of female offspring is preferred, e.g., dairy cattle or when it is desired to upgrade a herd.

The process of this invention can be employed to inseminate a variety of species of farm mammals, e.g., sheep, cows, pigs, goats, rabbits and horses. It is especially preferred for animals of the equine, bovine, and ovine species. Especially preferred as starting material is the semen from breeding stock individuals of a breed of a species whose semen is commercially especially valuable. Desirably, the fractionation process is initiated as promptly as possible after collection, e.g., within 1 to 4 hours. Frozen semen can be used as starting material after thawing. However, if frozen semen is used, the fractionated sperm is preferably used promptly after fractionation without refreezing.

In carrying out the fractionation process, the fractionation is continued until from about 10% to about 80%, preferably about 30% to about 50% of the motile sperm in starting semen migrates downwardly into the lower layer. A smaller percentage results in too small an increase in the incidence of male offspring to increase significantly the commercial value of the motile-sperm enriched portion of the semen for such purpose. Conversely, a larger percentage results in such a reduction in the populations of motile sperm in the motile-sperm depleted fraction that a reduction in the incidence of successful inseminations therefrom, even though the population of motile sperm in aliquots (straws) therefrom is retained at conventional levels.

The top and bottom layers obtained according to the process of this invention can be used immediately for inseminations or, preferably, are obtained from fresh semen and are then frozen until used.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

EXAMPLE 1

The following is a reproduction of the results of sheep herd tests conducted in Australia by I. G. White et al and reported "Reproduction in Sheep, supra".

Three Merino rams were electroejaculated two or three times each week for six weeks during September and October. Semen samples were assessed for motility of spermatozoa on a 0-5 scale and pooled if the score was four or higher. The pooled semen was extended at room temperature to a concentration of $200 \times 10^6$ spermatozoa per ml with diluent A: 300 mM fructose and 95mM citric acid. In test tubes (10 cm long 1.4 cm i.d.) the diluted semen (2 ml) was layered onto 6 ml of diluent B: 360 mM Tris, 33.3 mM glucose. 113.7 mM citric acid and 6% (w/v) BSA. After 2 hours holding at room temperature, the top (2 ml) and bottom (6 ml) portions of the column were collected in 10 ml centrifuge tubes and spun at 1000 g for 15 minutes: the supernatants were discarded and the spermatozoa from appropriate portions pooled and reconstituted with diluent A. The top portion contains about 50% of the starting motile sperm and the latter contains the remainder thereof. The suspensions of spermatozoa were recentrifuged, the supernatants discarded and the spermatozoa diluted 1:1 with diluent C: 360 mM Tris, 33 mM glucose, 113 mM citric acid, 18% (v/v) egg yolk and 6% (v/V0 glycerol The diluted spermatozoa were cooled to 5° C. in 1½ hours, pellet frozen on dry ice and stored in liquid nitrogen until insemination (Visser and Salamon 1973).

Eighty seven Merino ewes were treated with intravaginal sponges (30 mg Chronogest, Intervet Australia Pty Ltd, Robinson, T. J., 1965. Nature, London, 206, 39–41) for 12 days. At sponge removal each ewe received an intramuscular injection of 400 i.u. PMSG (Gravamed, Beresford Laboratories). The ewes were divided into two groups (a and b) and received two cervical inseminations (50 and 60 hours after sponge removal) with $100 \times 10^6$ motile spermatozoa from top (group a) or bottom (group b) portions of the BSA column.

Lambing data for ewes inseminated with spermatozoa from the top and bottom portions of the BAS columns are summarized in Table 1. Chi square comparisons of the numbers of male lambs after inseminating spermatozoa from the top and bottom of the BSA column showed a significant difference (P<0.01), as did comparisons of the numbers of female lambs (p<0.01). There was no significant difference in fertility of ewes inseminated with sperm from the top and bottom portions of the columns.

TABLE 1

Lambing following insemination of spermatozoa from the top and bottom of BSA columns.

| BSA column portion | No. ewes treated | No. lambed (%) | No. males (%) | No. females (%) |
|---|---|---|---|---|
| Top | 44 | 21 (47.7) | 8 (36.4) | 14 (63.3) |
| Bottom | 43 | 25 (58.1) | 18 (75.0) | 6 (25.0) |

The results of this experiment showed that ewes inseminated with spermatozoa from the bottom portion of the BSA column produced more male, and correspondingly fewer female lambs, than did spermatozoa from the top portion. Thus the Ericsson et al (Ericsson, R. J., Langevin, C. N. and Nishino, M., 1973. Nature, London, 246, 421–424) technique modified for ram spermatozoa, raises the possibility of separating X and Y chromosome bearing spermatozoa populations in the sheep. Unfortunately, it is not possible to identify these two types of sperm in the semen of the ram or other domestic species although the Y chromosome of human sperm can be stained with quinacrine (Barlow, P. and Vosa, C. G., 1970. Nature, London, 226, 961-962). The additional beneficial effects of this separation procedure observed in other species are increased sperm motility, reduced seminal debris and perhaps reduced sperm with abnormal morphology (Ericsson, R. J. and Glass, R. H., 1982. In Amann, R. P. and Seidel, G. E., Prospects for Sexing Mammalian Sperm, Colorado Association of University Press, Boulder, 201-211).

EXAMPLE 2

Follow the procedure of Example 1 with dairy cows employing semen from a breeding stock bull (dairy breed, e.g., Holstein). Use liquid nitrogen stored aliquots of sperm from the bottom layer, each of which contain, upon thawing, about $(10) \times 10^6$ motile sperm to artificially inseminate dairy cows (e.g., Holstein, Brown Swiss, Jersey) whose offspring are scheduled for veal or beef production. Use corresponding aliquots from the top layer containing, upon thawing, the same number of motile sperm to artificially inseminate dairy cows whose offspring are scheduled for herd building.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of artificially inseminating a plurality of animals with aliquots of semen from a breeding stock individual of the species, each of which contains a population of motile sperm large enough to ensure successful artificial insemination therewith, which comprises the steps of:

(a) fractionating the collected semen into a first fraction from which the immotile sperm and non-sperm components have been separated, containing from about 10% to about 80% of the motile sperm of the semen, suspended in a liquid vehicle which is physiologically acceptable to the sperm and for artificial insemination, and into a second fraction, containing the remainder of the motile sperm thereof, also suspended in a liquid vehicle which is physiologically acceptable to the sperm and for artificial insemination by the steps of (i) maintaining at least the sperm portion of progressively motile sperm-containing semen, either as such or suspended in an aqueous suspending vehicle physiologically acceptable to the sperm, as an upper layer in vertical interfacial contact, at a temperature at which the motile sperm are motile, with a lower discrete layer of a first aqueous contacting medium physiologically acceptable to the sperm in that the motile sperm migrate downwardly at a slower rate than in the upper layer, until a portion only of the motile sperm of the semen having migrated downwardly into the contacting medium, thereby producing a contacting medium containing a higher proportion of Y to X sperm than in the starting sperm, thereby producing in said upper laer a first portion of the second fraction of sperm and (ii) repeating the step at least once, employing in the upper layer the motile sperm which have migrated to the first aqueous contacting medium and as the lower layer a second aqueous contacting medium physiologically acceptable to the sperm and in which the motile sperm migrate downwardly at a slower rate than in the first contacting medium, thereby producing in the lower layer the first fraction of sperm, and in the upper layer a second portion of the second fraction of sperm;

(b) dividing the first fraction of sperm into a plurality of aliquots, each of which contain a population of motile sperm largel enough to ensure a pregnancy when used for an artificial insemination;

(c) dividing the second fractions of sperm into a plurality of aliquots, each of which contain a population of motile sperm large enough to ensure a pregnancy when used for an artificial insemination;

(d) artificially inseminating a plurality of individuals of that species in which a predominance of male off-spring is desired with the aliquots of the first fraction of sperm; and (e) artificially inseminating a plurality of individuals of that species in which a predominance of male off-spring is not a desired objective with the aliquots of the second fraction of sperm.

2. A process according to claim 1, wherein in Step (e), simultaneous ovulation in the individual animals has been induced hormonally.

3. A process according to claim 1, wherein the first fraction contains about 30 to about 80% of the motile sperm of the starting semen.

4. A method according to claim 1, wherein the second fraction contains the immotile sperm and non-sperm components of the original semen.

5. A method according to claim 1, wherein the second fraction is separated from the immotile sperm and non-sperm components of the original semen.

6. A method according to claim 1, wherein the species of animal is bovine.

7. A method according to claim 1, wherein the species of animal is ovine.

8. A method according to claim 1, wherein the thus-obtained aliquots of sperm are stored in a frozen state prior to use at a temperature and under conditions at which the sperm are storage stable.

9. A method according to claim 1, wherein in Step (d) simultaneous ovulation in the individuals has been induced hormonally, wherein the first fraction contains about 10 to about 50% of the motile sperm of the starting semen, wherein the second fraction contains the immotile sperm and non-sperm components of the original semen, and wherein th species of animal is bovine.

10. A method according to claim 9, wherein the species of animal is bovine.

11. A method according to claim 9, wherein the species of animal is ovine.

12. A method according to claim 1, wherein the second fraction contains about 50% of the motile sperm of the starting semen.

13. A method according to claim 9, wherein the second fraction contains about 50% of the motile sperm of the starting semen.

14. A method according to claim 1, wherein the starting semen is fresh in frozen semen; and wherein the sperm fractions obtained in step (a) are, prior to being divided into aliquots in steps (b) and (c), frozen and stored at liquid nitrogen temperature.

15. A method according to claim 14, wherein prior to being frozen and stored at liquid nitrogen temperature, the sperm fractions obtained in step (a) are centrifuged, separated from their respective aqueous contacting media and resuspended in fresh aqueous vehicle physiologically acceptable to the sperm.

* * * * *

UNITED STATES PATENT AND TRADEMARK OFFICE
CERTIFICATE OF CORRECTION

PATENT NO. : 4,764,373
DATED : August 16, 1988
INVENTOR(S) : Ronald J. Ericsson

It is certified that error appears in the above-identified patent and that said Letters Patent is hereby corrected as shown below:

Column 7, Claim 1, Line 2:

should read: --producing in said upper layer a first portion of the--

Column 7, Claim 1, Line 16:

should read: --motile sperm large enough to ensure a pregnancy--

Column 8, Claim 9, Line 18:

should read: --nal semen, and wherein the species of animal is bovine--

Signed and Sealed this

Sixth Day of December, 1988

Attest:

DONALD J. QUIGG

*Attesting Officer*  *Commissioner of Patents and Trademarks*